(12) United States Patent
Koch et al.

(10) Patent No.: US 10,646,227 B2
(45) Date of Patent: May 12, 2020

(54) SYSTEMS AND METHODS FOR ACUTE TREATMENT TO LIMIT INTRACEREBRAL HEMORRHAGE GROWTH

(71) Applicant: Cerepeutics, LLC, Miami Beach, FL (US)

(72) Inventors: Sebastian Koch, Miami Beach, FL (US); Max Pierre Mendez, Miami, FL (US)

(73) Assignee: Cerepeutics, LLC, Miami Beach, FL (US)

(*) Notice: Subject to any disclaimer, the term of this patent is extended or adjusted under 35 U.S.C. 154(b) by 199 days.

(21) Appl. No.: 15/854,547

(22) Filed: Dec. 26, 2017

(65) Prior Publication Data
US 2018/0185030 A1 Jul. 5, 2018

Related U.S. Application Data

(60) Provisional application No. 62/440,318, filed on Dec. 29, 2016.

(51) Int. Cl.
A61B 17/12 (2006.01)
A61B 17/00 (2006.01)

(52) U.S. Cl.
CPC .... *A61B 17/12036* (2013.01); *A61B 17/1204* (2013.01); *A61B 17/1214* (2013.01); *A61B 17/12109* (2013.01); *A61B 17/12131* (2013.01); *A61B 17/12136* (2013.01); *A61B 17/12172* (2013.01); *A61B 17/1215* (2013.01); *A61B 17/12177* (2013.01); *A61B 2017/00292* (2013.01); *A61B 2017/00778* (2013.01); *A61B 2017/00853* (2013.01);
(Continued)

(58) Field of Classification Search
CPC ....... A61B 17/12045; A61B 17/12136; A61M 2025/1052; A61M 2025/1097
See application file for complete search history.

(56) References Cited

U.S. PATENT DOCUMENTS 5,470,314 A 11/1995 Walinsky
6,136,025 A 10/2000 Barbut et al.
(Continued)

FOREIGN PATENT DOCUMENTS

DE 10102045 A1 1/2003
WO WO20008/058017 A2 5/2008

*Primary Examiner* — Martin T Ton
(74) *Attorney, Agent, or Firm* — Gordon & Jacobson, P.C.

(57) ABSTRACT

A method for the hemostasis of perforating and bleeding vessel related to intracerebral hemorrhage (ICH) includes navigating an occlusion device into a parent artery and then deploying the occlusive device to transiently occlude bleeding vessels to reduce blood flow and local blood pressure until hemostasis is achieved, while maintaining flow within the parent artery. Embodiments of the occlusion device include a catheter, an expandable member sized for insertion into the mid-cerebral artery (MCA) and having a length sufficient to occlude at least one ostia of the lenticulostriate arteries (LSA), with a flow path for blood provided from a proximal side of the expandable member to a distal side of the expandable member, and a semi-permeable contacting member about the expandable member and adapted to be in contact with a wall of the MCA adjacent the ostia, the semi-permeable member permitting a reduce flow of blood through the ostia.

15 Claims, 12 Drawing Sheets

(52) U.S. Cl.
CPC ........... *A61B 2017/00893* (2013.01); *A61B 2017/12004* (2013.01); *A61B 2017/1205* (2013.01)

(56) References Cited

U.S. PATENT DOCUMENTS

| | | |
|---|---|---|
| 6,183,492 B1 | 2/2001 | Hart et al. |
| 6,386,202 B1 | 5/2002 | Frazee |
| 7,306,619 B1 | 12/2007 | Palmer |
| 7,374,561 B2 | 5/2008 | Barbut |
| 7,468,027 B2 | 12/2008 | Barbut et al. |
| 7,879,067 B2 | 2/2011 | Galdonik et al. |
| 7,927,346 B2 | 4/2011 | VanCamp et al. |
| 7,993,324 B2 | 8/2011 | Barbut |
| 8,221,383 B2 | 7/2012 | Barbut |
| 9,364,432 B2 | 6/2016 | Macdonald et al. |
| 2006/0047262 A1 | 3/2006 | Barbut et al. |
| 2011/0152998 A1* | 6/2011 | Berez ............... A61F 2/82 623/1.15 |
| 2011/0172697 A1 | 7/2011 | Jonsson |
| 2012/0041460 A1 | 2/2012 | Ferrera et al. |
| 2012/0095489 A1* | 4/2012 | Rudakov ......... A61B 17/12031 606/191 |
| 2013/0269692 A1 | 10/2013 | Barbut et al. |
| 2014/0155981 A1 | 6/2014 | Ferrera et al. |
| 2014/0336690 A1* | 11/2014 | Zhadkevich .... A61M 25/10184 606/194 |
| 2016/0066932 A1* | 3/2016 | Root ............... A61B 17/12036 606/194 |
| 2016/0082178 A1* | 3/2016 | Agah .................. A61M 5/007 600/435 |

* cited by examiner

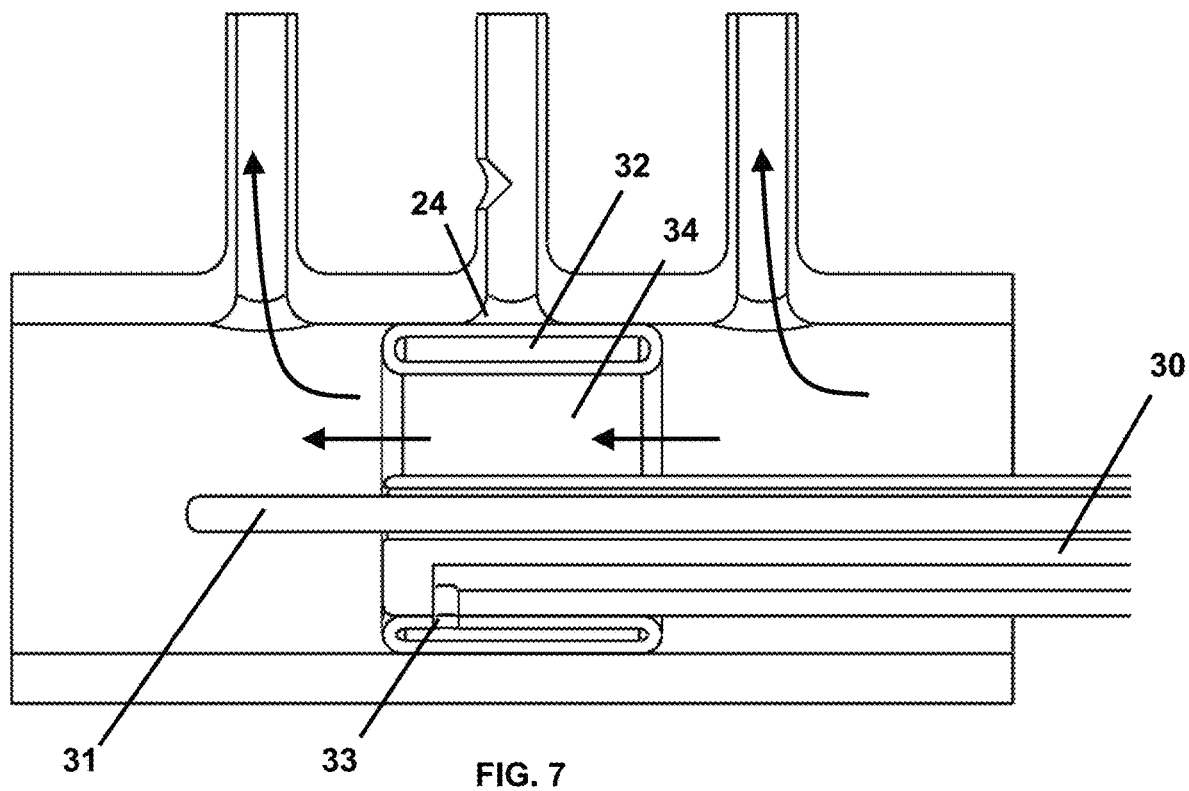
FIG. 7
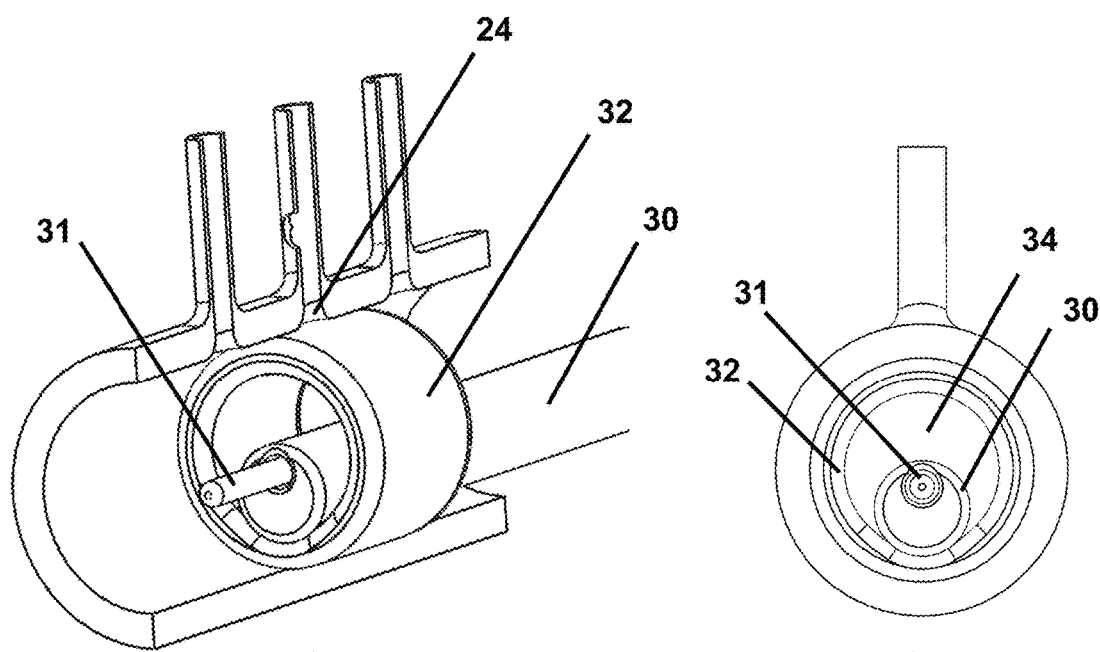
FIG. 8
FIG. 9

FIG. 22
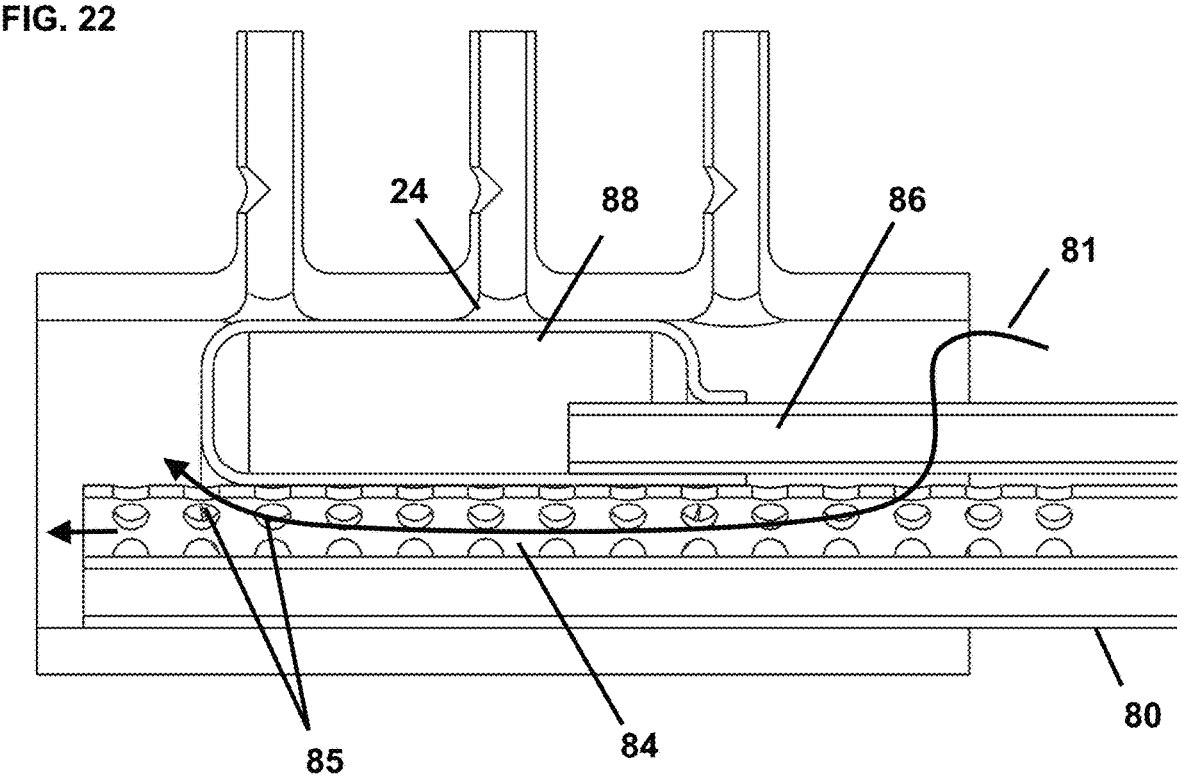
FIG. 23
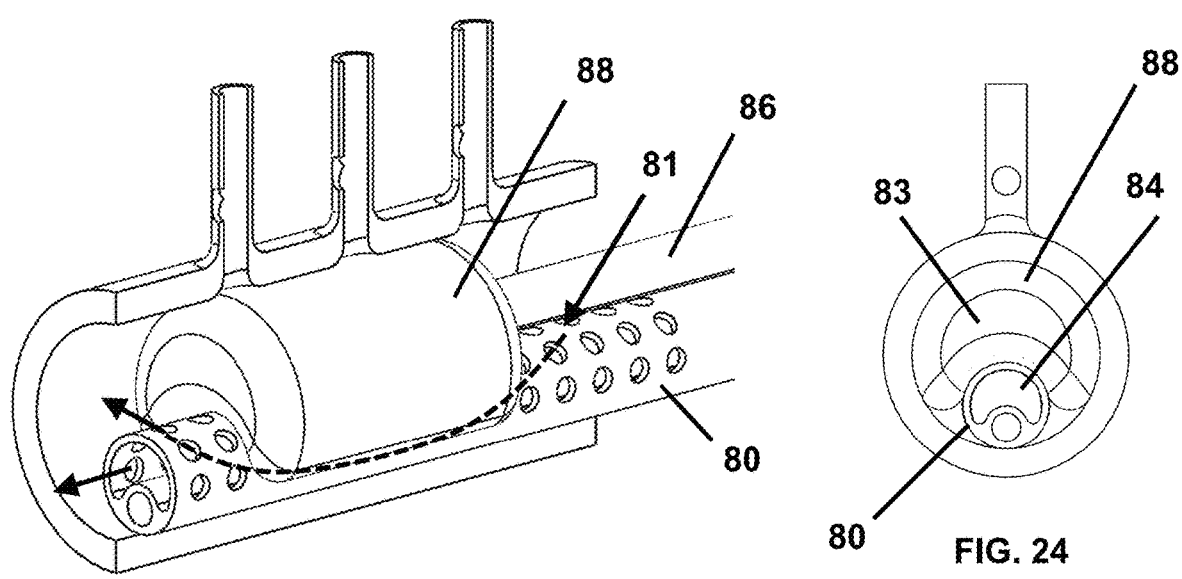
FIG. 24

SYSTEMS AND METHODS FOR ACUTE TREATMENT TO LIMIT INTRACEREBRAL HEMORRHAGE GROWTH

CROSS-REFERENCE TO RELATED APPLICATION

This application claims benefit to U.S. Provisional Ser. No. 62/440,318, filed Dec. 29, 2016, which is hereby incorporated by reference herein in its entirety.

BACKGROUND OF THE INVENTION

1. Field of the Invention

The present invention lies in the field of intravascular hemostatic devices. This invention relates generally to catheter based devices and methods for the cessation of hemorrhage in vessels. The invention also relates to delivery systems and mechanisms for such devices as well as devices that reduce procedural complexities and risks.

2. State of the Art

Strokes, also known as Cerebral Vascular Accidents (CVAs) affect nearly 800,000 individuals every year in the United States alone, leaving the effected with a significantly high morbidity and mortality rate. Of these 800,000 CVAs, 80% are caused by ischemia which is the disruption of blood flow due to a blockage. The other 20% are hemorrhagic in nature which is a significant bleeding within the brain or skull, causing both ischemia and pressure induced brain damage. Of the two major types, hemorrhagic strokes are far more difficult to treat and current methods are relatively invasive. Increased difficulty in treatment is caused by the large amount of cases (~80% of hemorrhagic strokes) that occur due to hemorrhage within the brain. There is currently no treatment, medical or surgical, for this type of hemorrhage. A prime example is a hemorrhage from the Lenticulostriate Arteries (LSA) located within the Putamen region of the brain, generally known as an Intracerebral Hemorrhage (ICH). These arteries are extremely small and variable in anatomy, and are typically known as perforator vessels (i.e. vessels that travel within large tissue structures) that also supply the thalamus, cerebellum and pons. Due to their anatomy, they are near impossible to access directly via non-surgical means such as neurointervention.

Currently there are no interventional devices to treat hemorrhaging perforating vessels such as the LSAs nor indirect intervention by way of their parent artery, the Middle Cerebral Artery (MCA). The vast majority of existing treatment options could create hemostasis by full occlusion of the MCA vessel, however this would cause ischemia downstream, effectively creating an additional ischemic stroke in tandem with the hemorrhagic stroke being repaired. This is an unacceptable risk.

In summary, while surgical methods do exist for the treatment of other types of hemorrhagic stroke, there are no solutions for smaller penetrating vessels leading to ICH such as, but not limited to, the LSA.

SUMMARY OF THE INVENTION

The invention provides systems and methods for treatment of acute stroke to reduce ICH expansion by using devices to reduce blood flow into hemorrhaging vessels and reducing the blood pressure acting on hemorrhaging vessels in a manner that reduces bleeding and ultimately seals bleeding vessels.

Although the invention is illustrated and described herein as embodied in systems and methods of limiting ICH, it is, nevertheless, not intended to be limited to the details shown because various modifications and structural changes may be made therein without departing from the spirit of the invention and within the scope and range of equivalents of the claims. By way of example, the structure of the individual hemostatic devices, alone or in combination with the deployment systems taught herein, can be used to seal and provide temporary hemostasis at an ostium or an aperture in a single tissue wall, including in a vessel. Additionally, well-known elements of exemplary embodiments of the invention will not be described in detail or will be omitted so as not to obscure the relevant details of the invention.

A method for the hemostasis of perforating and bleeding vessel related ICH includes: navigating an occlusion device in a catheter-based endovascular approach into a parent artery and then deploying the occlusive device in such a manner that the bleeding vessels are transiently occluded until hemostasis is achieved, while maintaining flow within the parent artery. The bleeding arteries are reduced in flow or occluded at their ostia that has several biological effects. Occlusion of the penetrating arteries prevents blood from entering the artery and reducing the blood pressure forces acting on those arteries, essentially eliminating the possibility of any further blood loss. While occlusion may be one method of treatment, it may be advisable to retain some blood flow through the bleeding vessel. Therefore, the system is adapted to achieve a temporary reduction of blood flow of preferably at least 50%, and potentially 50-70%. The goal is to treat intracerebral hemorrhage by limiting hematoma growth. The temporary occlusion also effectively reduces the mechanical blood pressure forces acting at the site of arterial rupture and thereby less pressure drives blood into brain tissue. This leads to a reduction of blood flow and causing flow to become stagnant, which triggers a coagulation cascade leading to thrombosis that seals the bleeding vessels. Once adequate resolution of hemorrhage has been identified, the operator then recaptures or removes the device from the access route. Specifically, in regards to hemorrhaging LSA for example, the occlusion device can be navigated into the MCA then deployed up against LSA ostia while maintaining adequate blood flow through the MCA. Additionally, this method can be used to create hemostasis and support the repair of vessels with natural or iatrogenic perforations.

Thus, in one embodiment, all blood flow to the hemorrhaging vessel is occluded. In another embodiment, partial occlusion of the origins of the perforating arteries is provided to allow continued, but reduced blood flow reduced flow to the perforator territory (flow diversion). This serves to meet the delicate balance between inducing hemostasis, but yet, preventing ischemia. Partial occlusion may be accomplished by covering the ostia with a semi-permeable membrane. All of the above is accomplished while continued blood flow through the parent artery is maintained to prevent ischemia (lack of blood flow) downstream.

Additional advantages and other features characteristic of the present invention will be set forth in the detailed description that follows and may be apparent from the detailed description or may be learned by practice of exemplary embodiments of the invention. Still other advantages of the

BRIEF DESCRIPTION OF THE DRAWINGS

FIG. 7 is a diagrammatic cross-sectional view similar to FIG. 6 that includes an occlusive hollow balloon;

FIG. 8 is a diagrammatic, isometric and partially cross-sectioned view of FIG. 7;

FIG. 9 is a complete frontal view of FIG. 7;

FIG. 22 is a diagrammatic cross-sectional view similar to FIG. 6 that includes a flow-through catheter and an occlusive balloon catheter;

FIG. 23 is a diagrammatic, isometric and partially cross-sectioned view of FIG. 22;

FIG. 24 is a complete frontal view of FIG. 22;

DETAILED DESCRIPTION OF THE PREFERRED EMBODIMENTS

Figure 1:
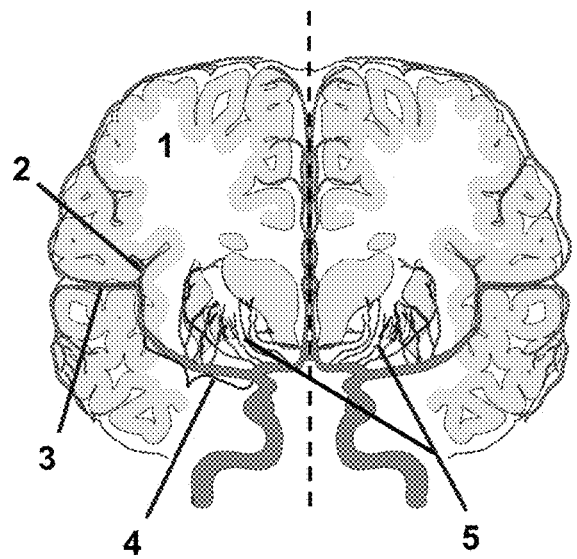
FIG. 1 is a coronal midplane view of the human cerebrovascular system.

Detailed embodiments of the systems and methods are disclosed herein; however, it is to be understood that the disclosed embodiments are merely exemplary of the systems and methods, which can be embodied in various forms. Therefore, specific structural and functional details disclosed herein are not to be interpreted as limiting, but merely as a basis for the claims and as a representative basis for teaching one skilled in the art to variously employ the systems and methods in virtually any appropriately detailed structure. Further, the terms and phrases used herein are not intended to be limiting; but rather, to provide an understandable description of the systems and methods. While the specification concludes with claims defining the features of the systems and methods that are regarded as novel, it is believed that the systems and methods will be better understood from a consideration of the following description in conjunction with the drawing figures, in which like reference numerals are carried forward.

Figure 2:
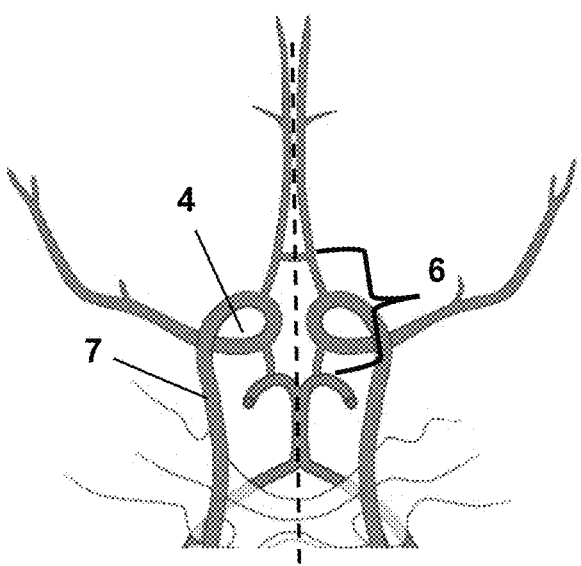
FIG. 2 is an axial view of FIG. 1.
Figure 3:
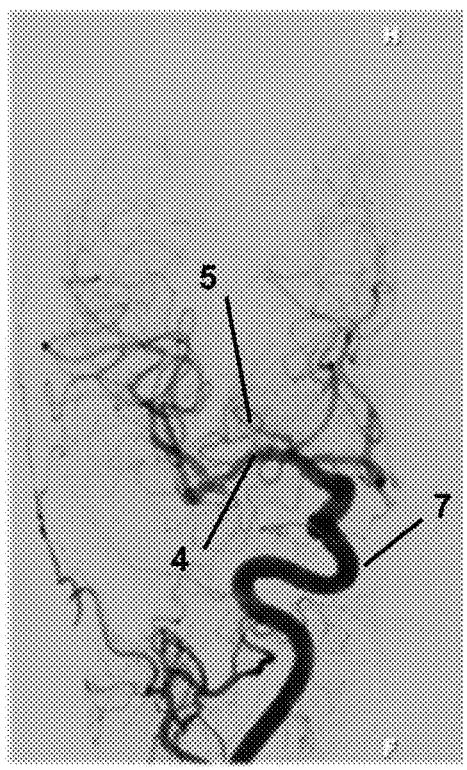
FIG. 3 is a fluoroscopic view similar to FIG. 1.

Described now are exemplary embodiments. Referring now to the figures of the drawings, FIG. 1 illustrates a coronal midplane view of the brain 1 and human cerebrovascular system including the distal portion of the mid-cerebral artery (MCA) 2, the anterior temporal artery 3, the proximal portion of the MCA 4 and lenticulostriate arteries (LSAs) 5. FIG. 2 is an axial view of FIG. 1 with the brain hidden and the Circle of Willis 6 shown. Also shown is an axial view of the MCA proximal portion, and the internal carotid artery 7. FIG. 3 is a fluoroscopic view of the cerebrovascular system shown during cerebral angiography. Also shown are the fluoroscopic views of the LSA 5, proximal MCA 4, and internal carotid artery 7.

Figure 4:
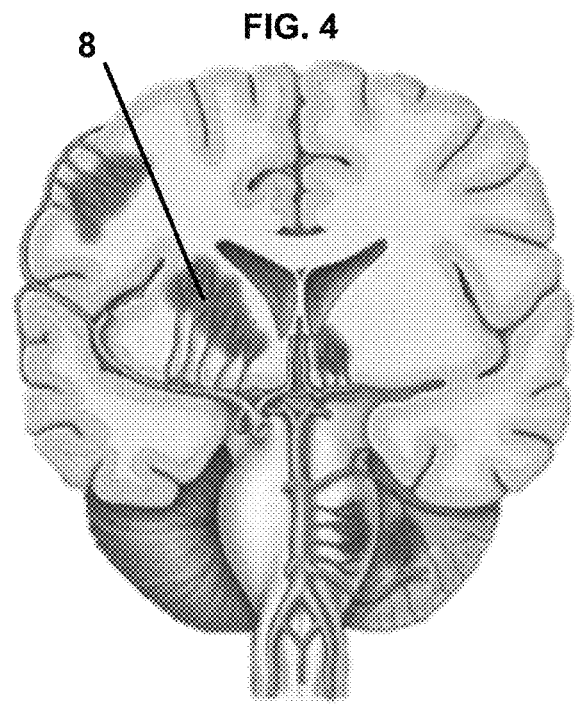
FIG. 4 is a coronal midplane view similar to FIG. 1 with major cerebrovascular arteries shown.

FIG. 4 is a coronal midplane view similar to FIG. 1 with major cerebrovascular arteries shown. Also shown is a region of ICH within the Putamen of the brain 8.

Figure 5:
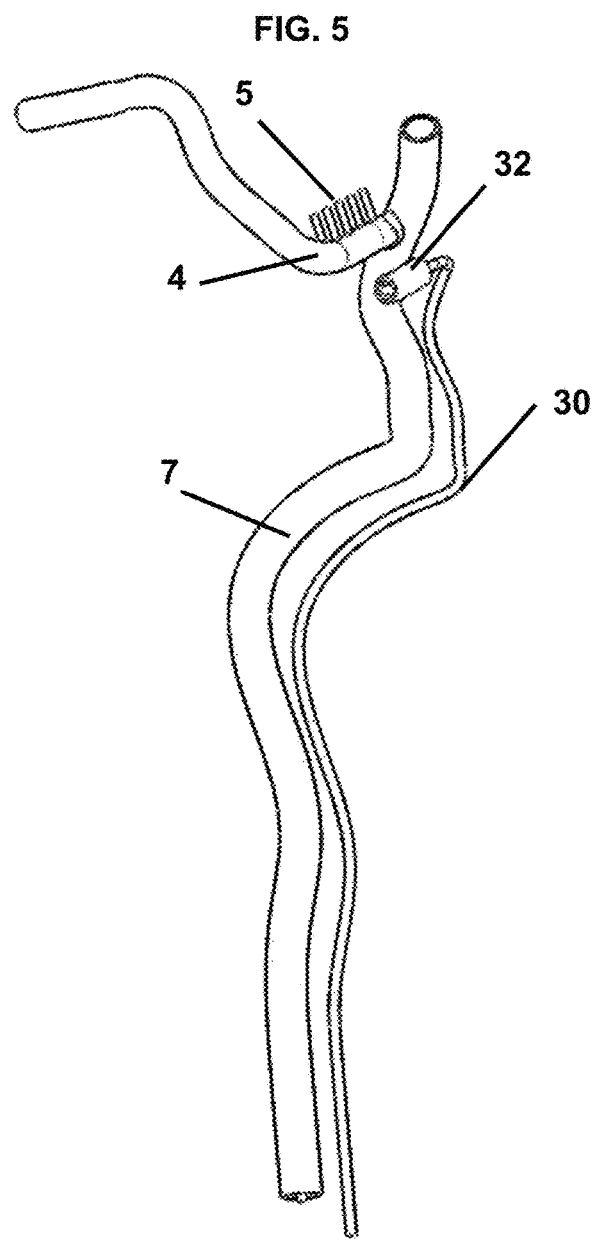
FIG. 5 is a diagrammatic isometric view of a vascular tract from Internal Carotid Artery to MCA and LSAs.

FIG. 5 is a diagrammatic isometric view of a vascular tract from Internal Carotid Artery 7 to MCA 4 and LSAs 5 with an overlaid catheter 30 that includes a distal expanding hollow balloon 32, as further described below.

Figure 6:
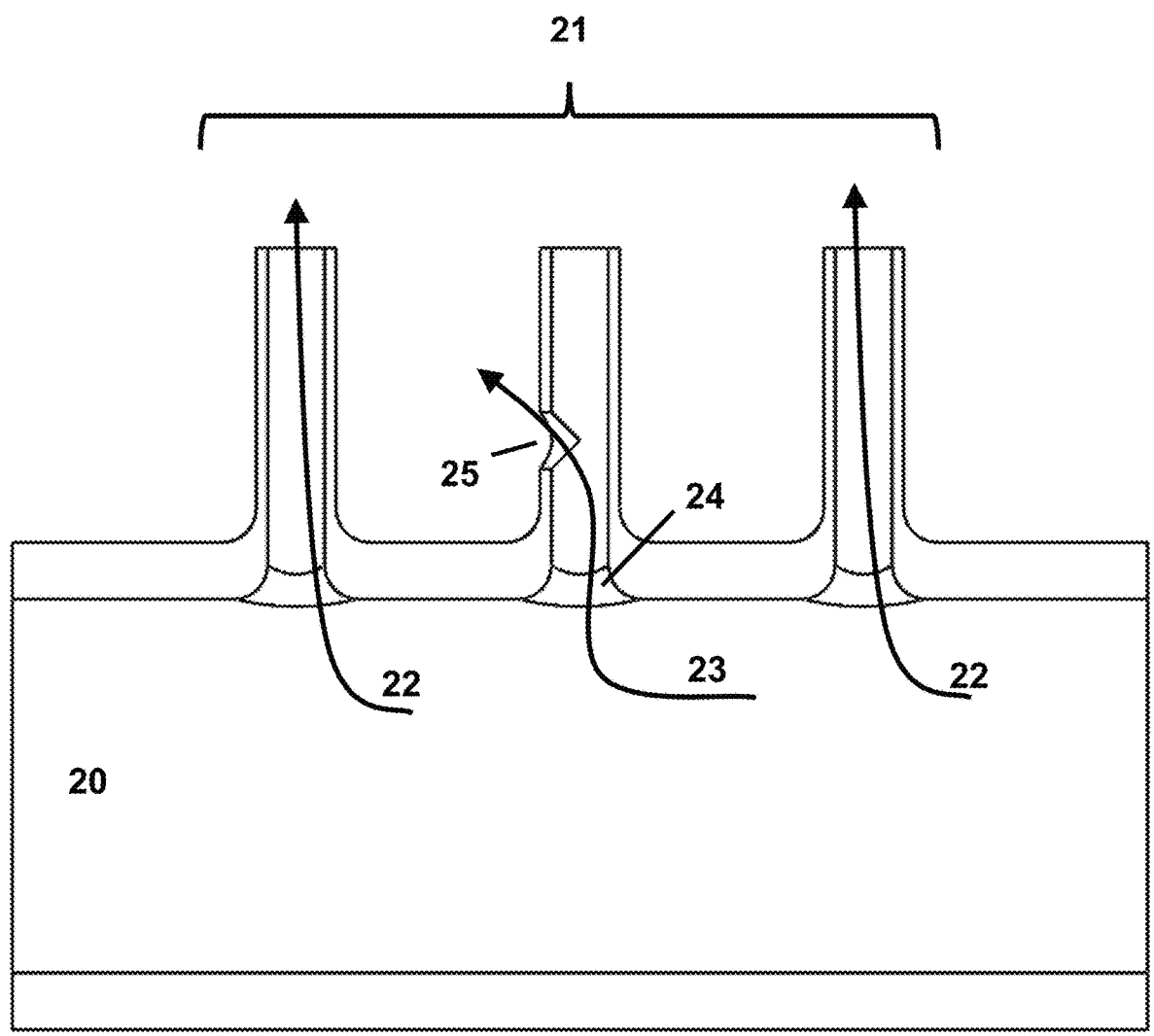
FIG. 6 is a diagrammatic cross-sectional view describing hemorrhaging LSA ostia.

FIG. 6 is a diagrammatic cross-sectional view of a MCA 20 and LSAs 21 with nominal flow path maintained within two LSAs 22. It also shows a hemorrhage path 23 that enters hemorrhaging LSA ostia 24 and exits at hemorrhage point 25.

FIGS. 7 through 9 illustrate a first embodiment of the occluding flow-through catheter device 30 delivered over a guidewire 31 with the hollow balloon 32 inflated through an inflation lumen 33. The balloon 32 is shown inflated against hemorrhaging LSA ostia 24 thereby occluding flow into hemorrhaging LSA while allowing flow through the central hollow portion 34 of the balloon 32.

The balloon 32 is pressurized to form an expanded cylindrical shape with a central conduit that allows blood flow without significant interruption. The overall structure of this balloon can be described as a toroidal ("hollow") cylinder. Additionally, this entire structure is designed to allow for atraumatic deployment, tethering, and retrieval. The catheter may be constructed with a multi-lumen core, allowing for an independent conduit for infusion of the balloon while still enabling the passage of additional equipment such as a guidewire through the central lumen. Additionally, the catheter 30 can have a lumen for contrast injection used for angiographic seal and hemorrhage assessment. The balloon 32 can be made from compliant materials, non-compliant materials or a composite of both. An alternate configuration of the balloon is made from a semi-permeable material that allows for structural inflation as well as direct administration of inflation fluid that can contain pharmacologic solutions to reduce hemorrhaging and improve hemostasis. In use specific to occlusion of LSAs from the MCA, the balloon can be formed to have a maximum diameter of about 4 mm at an inflation pressure range of 2-4 ATM and a length around 15 mm. The length of occlusion devices can vary between the length required to occlude one or a plurality of branch vessel ostia. The balloon can be contained within a spring like structure that assists in collapsing and keeping the balloon in a tight packed configuration against catheter.

Figure 10:
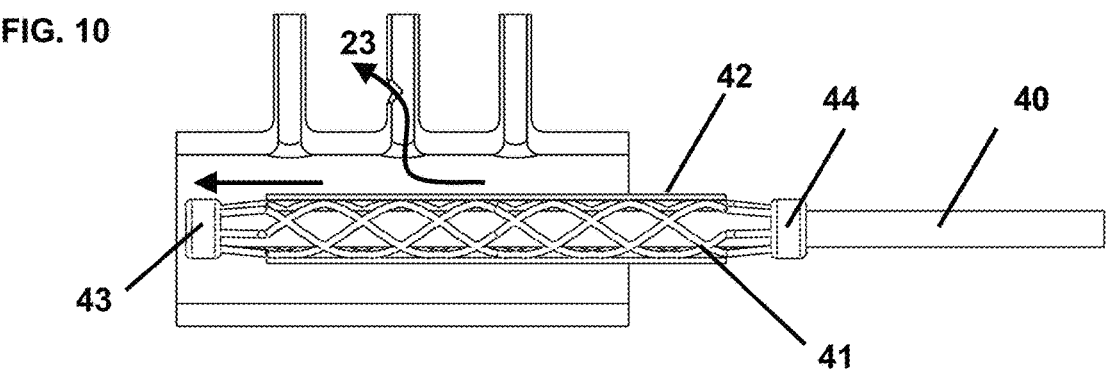
FIG. 10 is a diagrammatic partially cross-sectional view similar to FIG. 6 that includes a collapsed occlusive mesh structure.
Figure 11:
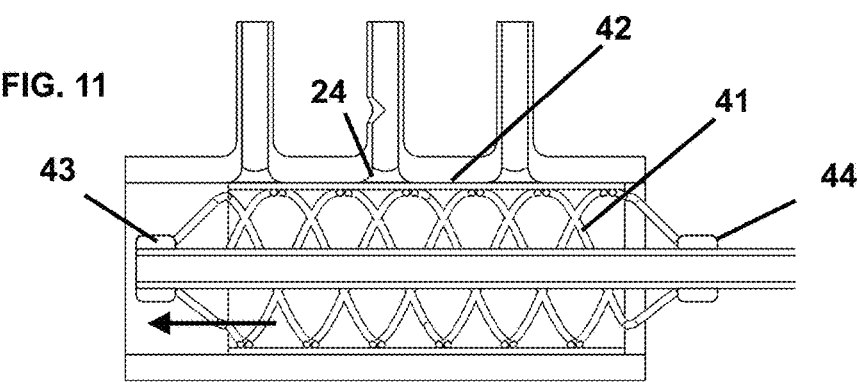
FIG. 11 is similar to FIG. 10 but demonstrates an expanded occlusive mesh structure.
Figure 12:
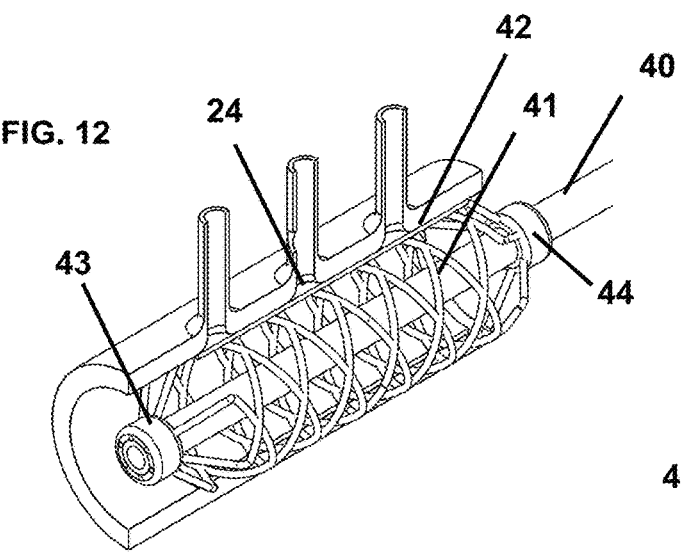
FIG. 12 is a diagrammatic, isometric and partially cross-sectioned view of FIG. 10.
Figure 13:
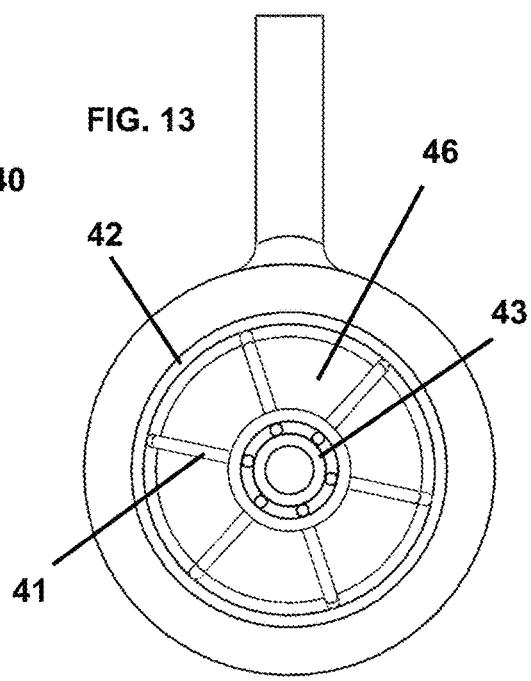
FIG. 13 is a complete frontal view of FIG. 10.

FIG. 10 illustrates a second embodiment of an occluding flow-through catheter device 40 in which a distal end of the catheter contains a mesh structure 41 in a collapsed state. The mesh structure is surrounding by a film 42 about its exterior. The film 42 may be hemostatic. The structure is grounded within a distal hub 43 and a proximal hub 44. FIG. 10 also shows a hemorrhage path 23 through an LSA. FIGS. 11 through 13 illustrates the mesh structure 41 in an expanded state, allowing apposition between the hemostatic film 42 and the hemorrhaging LSA ostia 24 thereby eliminating hemorrhaging path and allowing flow through its central hollow portion 46.

The mesh structural frame 41 can be comprised of a series of struts that can be expanded from a collapsed configuration via self-expansion, by a user driven deformation, or by a user activated shape memory deformation. In an embodiment, a proximal hub 44 may be longitudinally translated relative to the distal hub 43 expand and collapse the structure 41. The frame is expanded up against the surrounding vessel, allowing the occlusive material to create a seal against the branched vessel ostia. The frame material can be made from nitinol and the occlusive material can be made to fully occlude or allow partial perfusion using materials such as ePTFE, PET, or other polymers. A mechanized system can be used to allow precise control over user-driven frame expansion into vessels. Such mechanisms can be based on indexed screw threads or geared linear actuators that can be housed either at the distal end of the catheter or within the handle. This system allows for more precise expansion, contraction, and deployment of the entire device.

Figure 14:
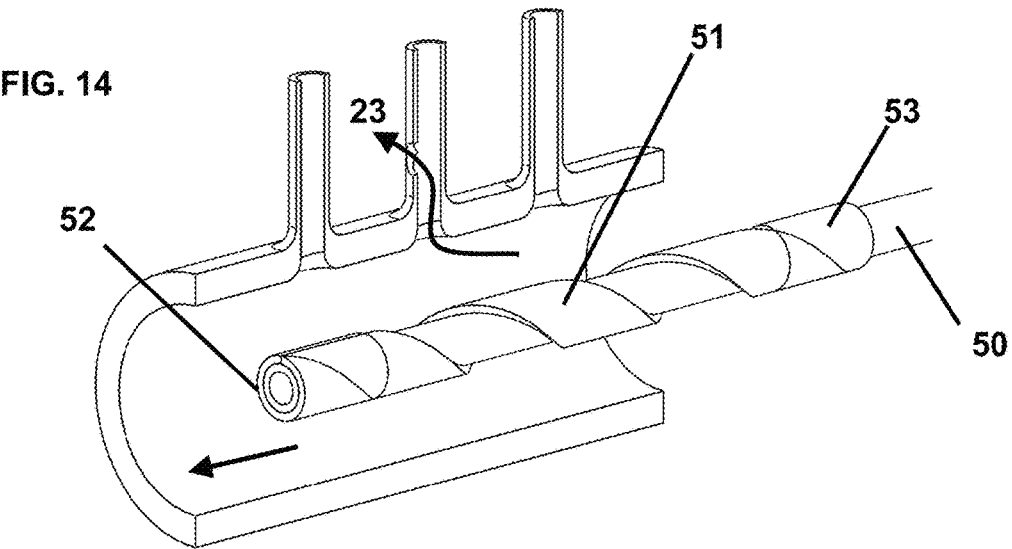
FIG. 14 is a diagrammatic, isometric and partially cross-sectioned view of a collapsed hemostatic ribbon.
Figure 15:
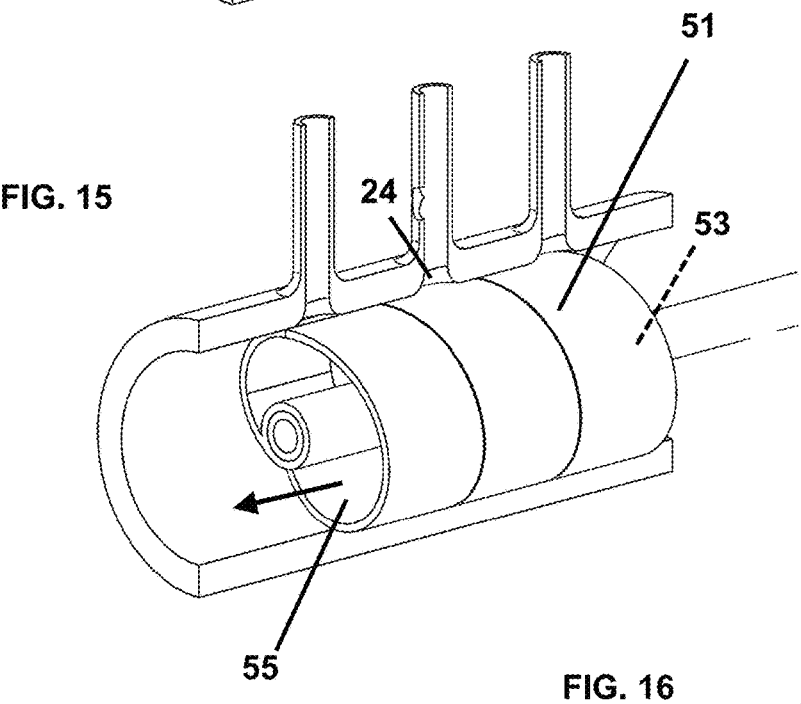
FIG. 15 is similar to FIG. 14 but demonstrates an expanded hemostatic ribbon.
Figure 16:
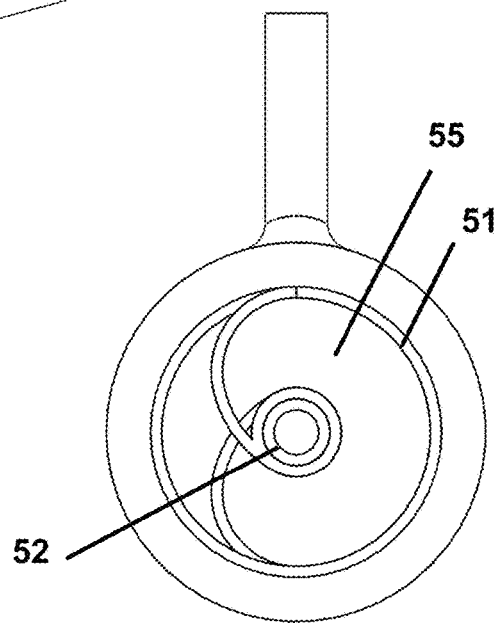
FIG. 16 is a complete frontal view of FIG. 14.

FIG. 14 illustrates a third embodiment of an occluding flow-through catheter device 50 in which a distal end of the catheter 50 is surrounded by a collapsed hemostatic ribbon 51 grounded within a distal hub 52 and proximal hub 53. The hemostatic ribbon 51 extends helically about the catheter 50. Turning to FIGS. 15 and 16, rotation and/or longitudinal displacement of distal and proximal hubs 52, 53 relative to each other expands the hemostatic ribbon 51 allowing apposition against hemorrhaging LSA ostia 24 thereby eliminating hemorrhaging path and allowing flow through its central hollow portion 55.

Figure 17:
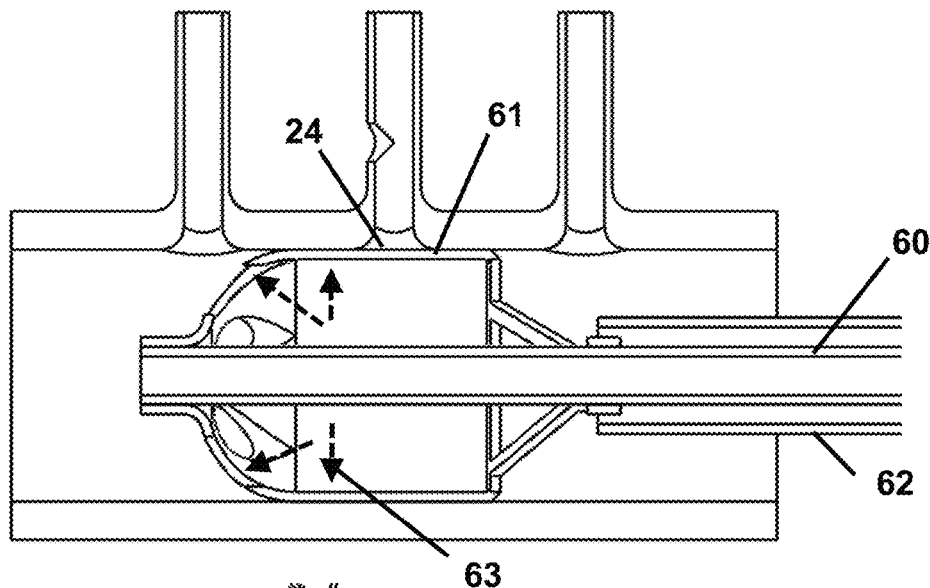
FIG. 17 is a diagrammatic cross-sectional view of a passive occlusive structure.
Figure 18:
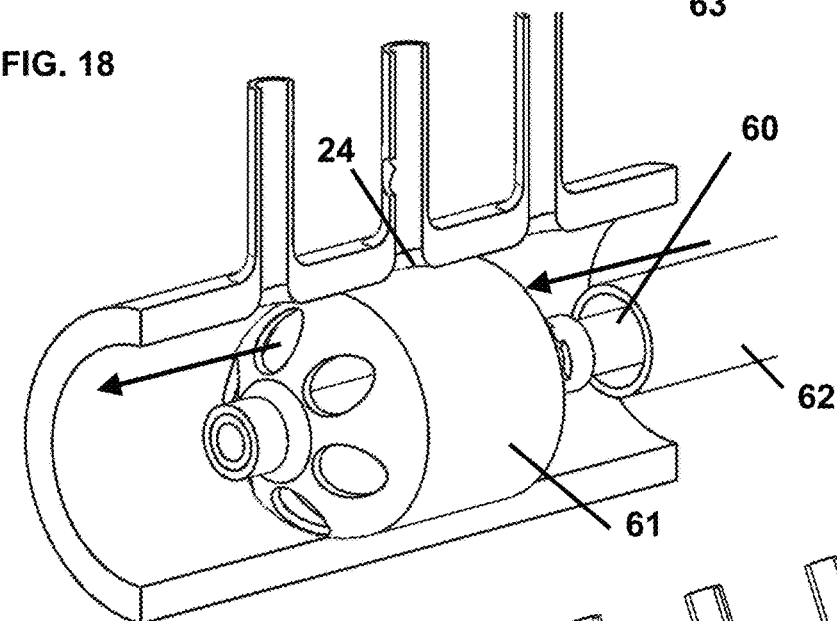
FIGS. 18 and 19 are diagrammatic, isometric and partially cross-sectioned views of FIG. 17.
Figure 19:
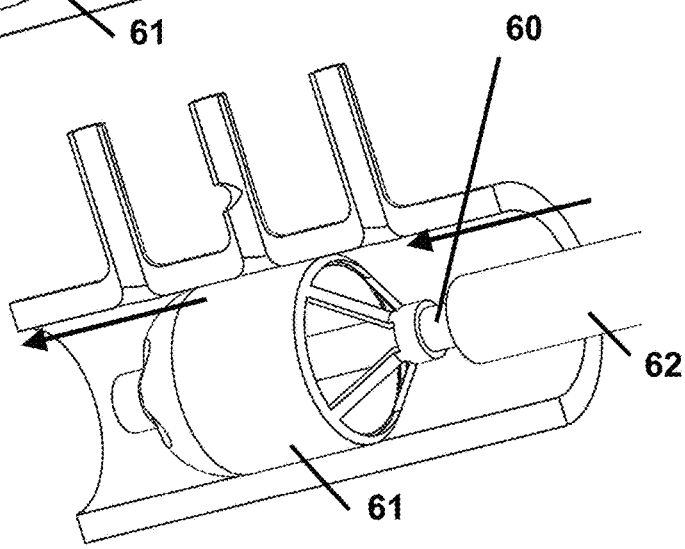

FIGS. 17 through 19 illustrate a fourth embodiment of an occluding flow-through catheter device 60 in which a flexible hemostatic material 61 is deployed out of a delivery tube 62 to appose a hemorrhaging LSA ostia 24 by hemodynamic forces 63 from flow within the structure. The structure can be non-self-expanding, non-operator driven, flexible and low profile. The structure can function similar to a "windsock" that allows flow through with some drag to create an expanded structure. The structure can be secured to a central core at its distal and proximal end to aid deployment and retrieval within a tube.

Figure 20:
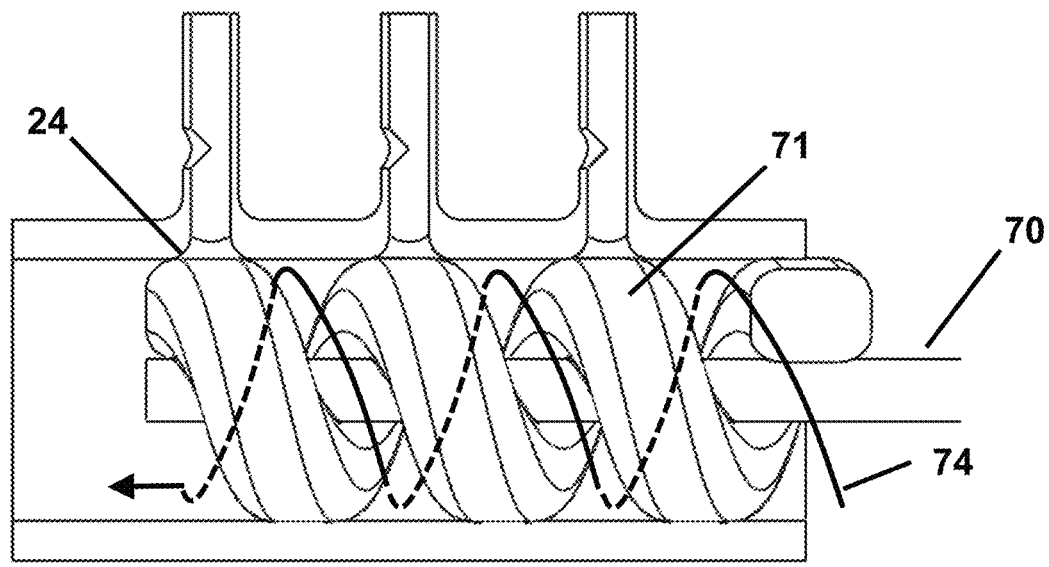
FIG. 20 is a diagrammatic partially cross-sectional view similar to FIG. 6 that includes an expanded occlusive helical structure.
Figure 21:
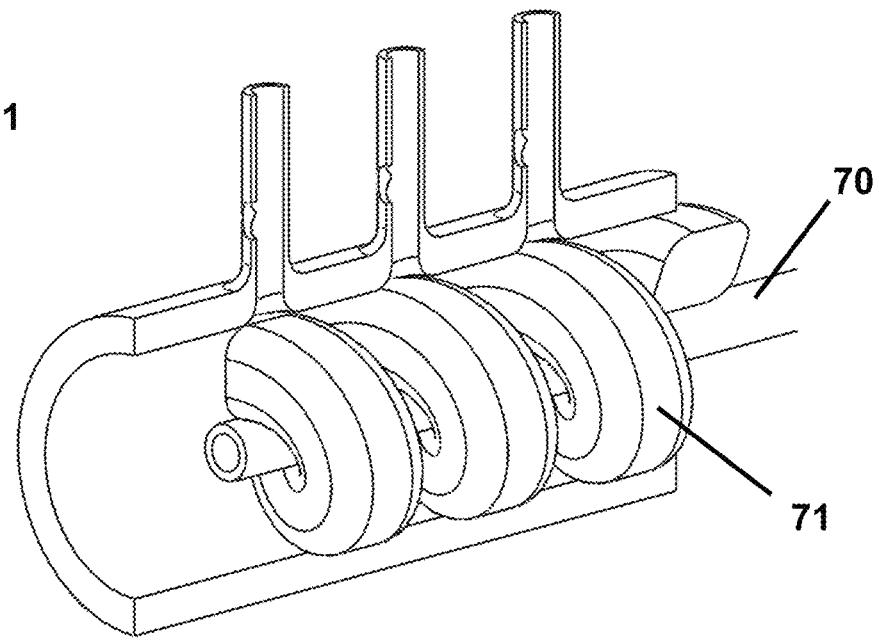
FIG. 21 is a diagrammatic, isometric and partially cross-sectioned view of FIG. 20.

FIGS. 20 and 21 illustrate a fifth embodiment of an occluding flow through catheter device 70 provided with an occlusive helical structure 71 at the distal end of the catheter that is aligned to occlude hemorrhaging LSA ostia 24. The valley of the helical structure defines its flow through path 74. In an embodiment, the helical structure does not rely on expansion and occlusion up to branched vessel ostia but creates a tortuous and flow restricting path between the parent vessel and branched vessel. In another embodiment, the helical structure is expanded radially from its center axis and creates both an outer occlusive helical band and a helical conduit allowing blood to flow in a helical but axial direction. The pitch of the helix is set to match the average distance between vessel ostia. Linear and rotational manipulation allows the user to selectively occlude ostia. The helical structure can be composed of a rigid but deformable occlusive material or a composite of a metallic frame and occlusive material. Alternatively, the helical structure can be an inflatable balloon that is either attached or not attached to a central core.

FIGS. 22 through 24 illustrate a sixth embodiment of a device having a flow-through tubular member 80 containing a central lumen 84 and side holes 85 to define a fluid passage 81. The device also includes a catheter 86 having at its distal end an inflatable parallel compliant balloon 88 that contours around the flow through tubular member 80. When the balloon is inflated, the device creates an occluded area 83 and a flow through area 84 (FIG. 24). Blood flow through the vessel is blocked, but fluid flow through the openings of the flow through catheter is permitted. The tubular member 80 may be a full-length catheter or a short segment. The tubular member 80 and catheter 86 may be either attached or independent. The expanded balloon 88 provides both the hemostatic apposition to the branched vessel ostia 24, as well as anchoring the catheters within the vessel.

Figure 25:
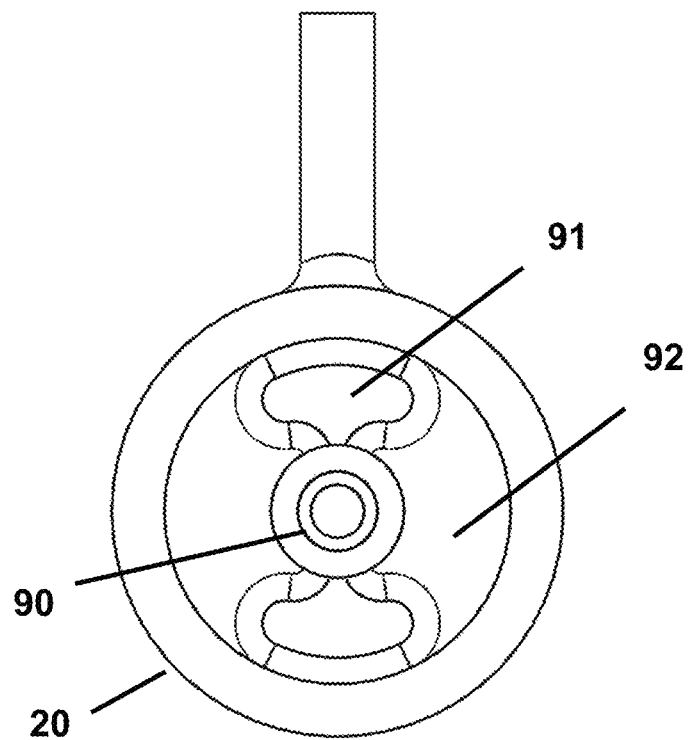
FIG. 25 is a complete frontal view of a catheter with an occlusive balloon catheter.
Figure 26:
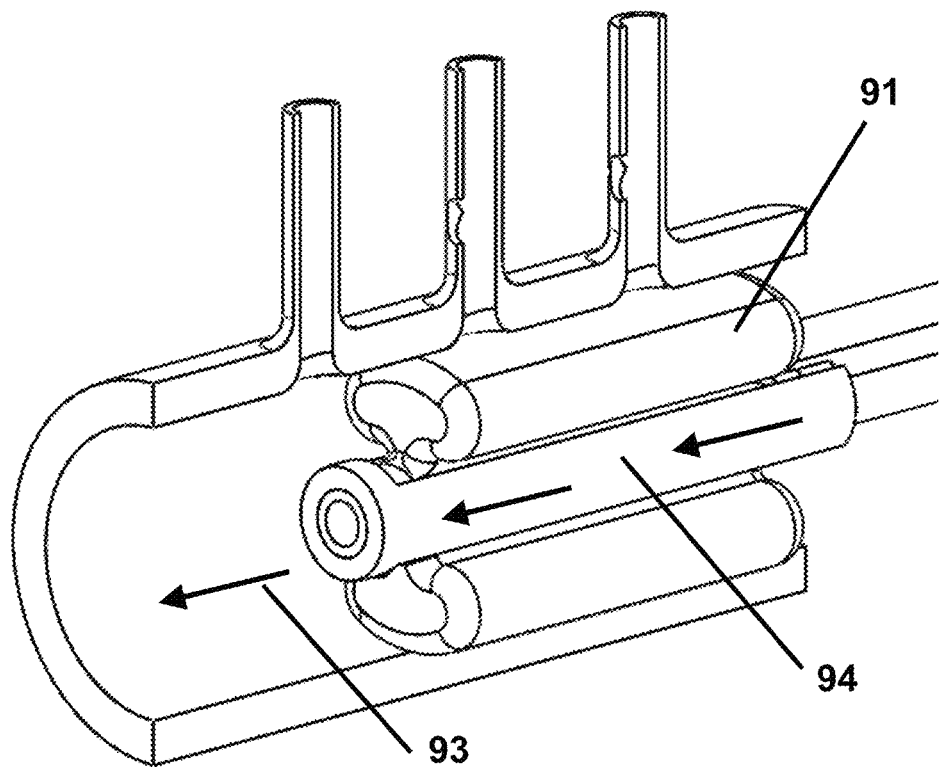
FIG. 26 is a diagrammatic, isometric and partially cross-sectioned view of FIG. 25.

FIGS. 25 and 26 illustrate a seventh embodiment of an occluding flow-through catheter device. The device includes a catheter 90 with one or more expanded balloon portion 91 within an MCA 20 and demonstrating a flow through area 92. The balloon portion 91 surrounding the catheter is constrained by an outer shield 94 that restricts balloon expansion in order to create a non-occlusive area. The balloon portion 91 may comprise a single shaped balloon, or multiple balloons. The balloon portion 91 is located radially and tangent to a central core. When inflated, the balloon portion provides both the hemostatic occlusion to the LSA ostia, as well as anchoring the catheters along the vessel wall. The balloon portion being arranged in a radial fashion creates areas of circumferential occlusion and areas that are unobstructed. The areas that are not obstructed create a passage to allow blood to flow throughout the parent vessel. This embodiment can be constructed by attaching individual cylindrical balloons around a central lumen or by one concentric cylindrical balloon that is restrained along its length in a radial fashion. Such restraint can be achieved by bonding the balloon to the central catheter, housing the balloon within the central catheter and allowing it to expand through open slots, or using other components to restrict the expansion of the balloon.

Figure 27:
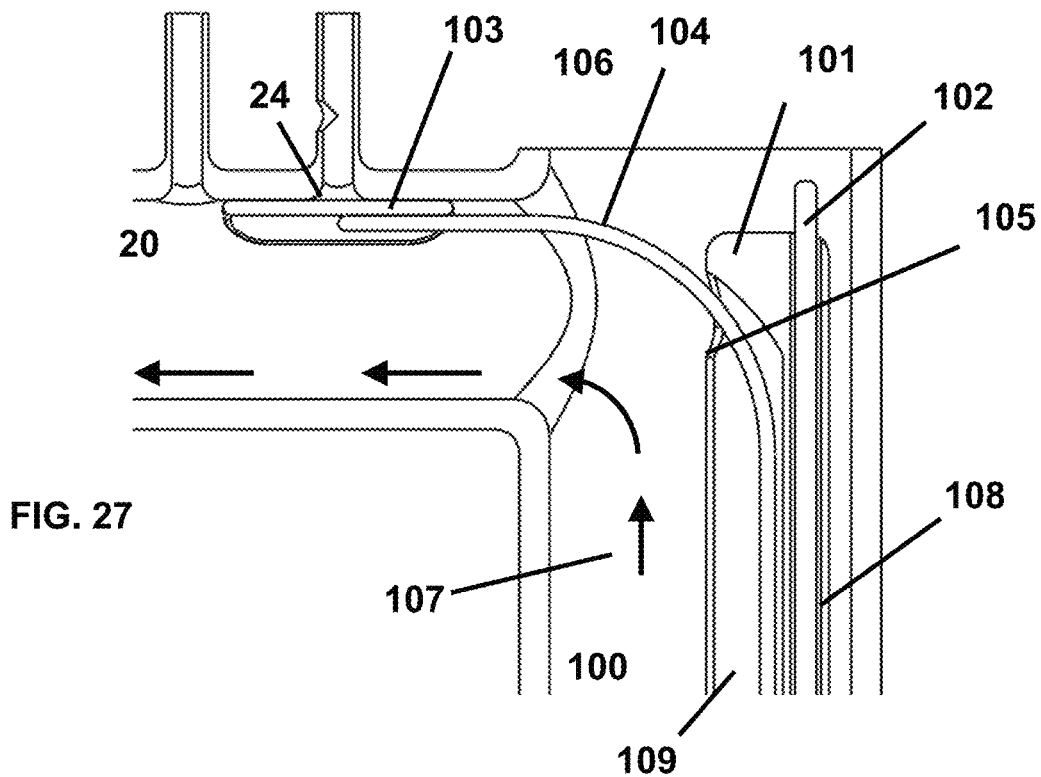
FIG. 27 is a diagrammatic cross-sectional view of an MCA and ICA containing an occlusive paddle catheter.
Figure 28:
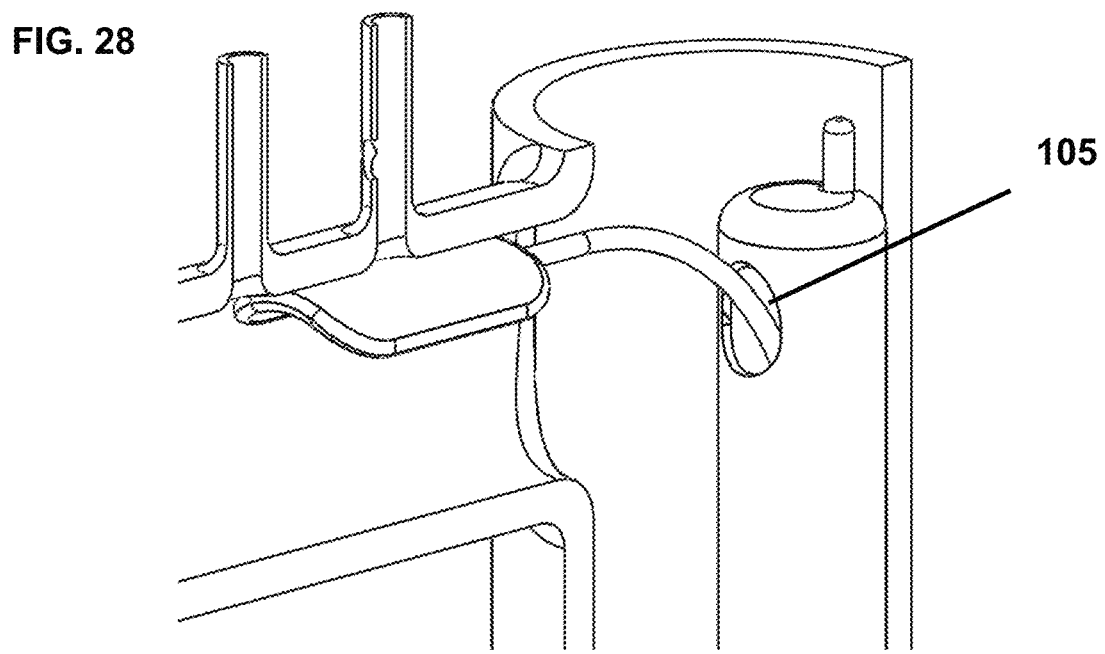
FIG. 28 is a diagrammatic, isometric and partially cross-sectioned view of FIG. 27.

FIGS. 27 and 28 illustrate an eighth embodiment of an occluding catheter device. The figures illustrate an MCA 20 and the internal carotid artery 100, the parent vessel of the MCA, and the catheter device 101. The catheter device includes a first lumen 108 over which the catheter device is advanced over a guidewire 102. The catheter device also includes a second lumen 109. An occlusive paddle 103 is attached to a spring-loaded connection member 104 that extends through the second lumen and exits through a guided side passage 105. The side passage 105 deflects the normally straight connection member into the MCA from the ICA and forces the paddle up against a hemorrhaging LSA ostia 24 to create occlusion. The system is low profile and retains a natural flow path 107 from the internal carotid artery 100 to the MCA 20.

The paddle can be inserted into an acutely branched vessel and positioned against hemorrhaging ostia. The occlusive paddle can be a passive or expandable structure and be forced up to the ostia by the spring-loaded connection member. The connection member can possess a shape-memory configuration that is beyond the circular profile of the catheter system, thereby forcing the paddle out in a radial direction. Alternatively, the paddle can be deployed from a proximal to parent vessel. For example, the paddle can be deployed from the ICA, into the MCA and positioned against LSA ostia. Another configuration can utilize a shaped catheter to create the spring-loaded force needed to force an occlusive structure up to a branched vessel ostia.

Figure 29:
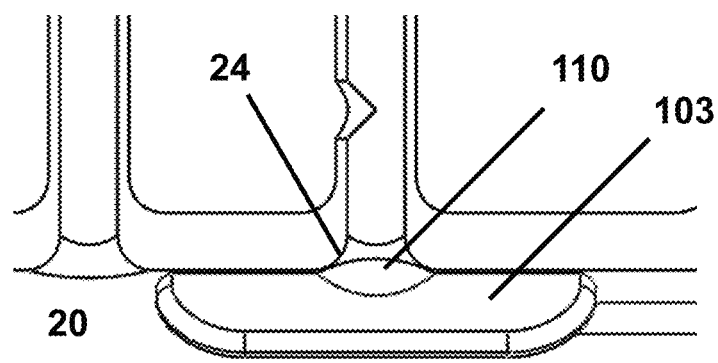
FIG. 29 is a diagrammatic partial cross-sectional view of an occlusive paddle with a self-centering dome.

An additional feature to improve the positioning of a structure against a branched vessel ostia is utilizing a spherical like geometry that matches the ostial cavity thereby creating a self-centering fit. This can be done for a single ostia structure or a chain similar with a "peapod" like shape. By way of example, as shown in FIG. 29, the paddle 103 contains a dome 110 that matches the ostial cavity thereby creating a self-centering fit. Self-centering can also be improved by using a structure formed with a low thickness profile and contain an ostial side that is convex and an opposing side that is concave to allow for a matching and parallel force area.

Figure 30:
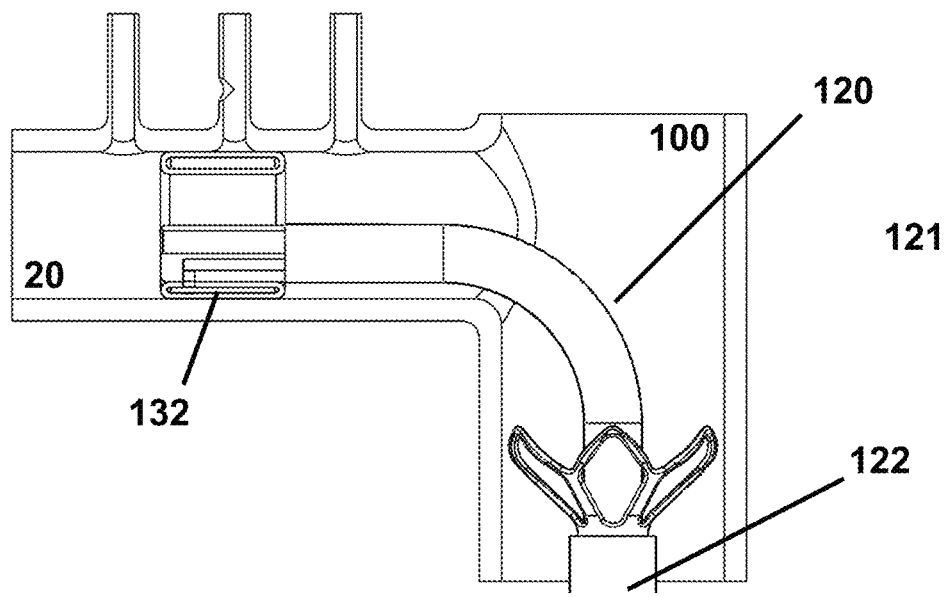
FIG. 30 is a diagrammatic cross-sectional view of an MCA and ICA with a grounded hollow balloon catheter.
Figure 31:
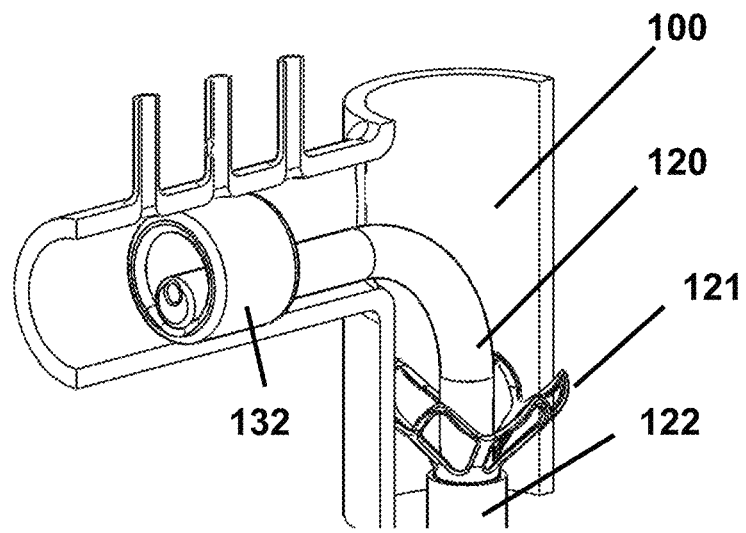
FIG. 31 is a diagrammatic, isometric and partially cross-sectioned view of FIG. 30.

FIGS. 30 and 31 illustrate a ninth embodiment of an occluding flow-through catheter device 120. The catheter device 120 includes a hollow expandable balloon 132 (similar to balloon 32). An expandable non-occlusive structure 121 is deployed within the ICA 100 to create an anchored grounding point. The catheter 120 is able to translate about the anchor point 121. The anchored grounding point can be deployed and recaptured by manipulating an outer tube 122. Other non-occlusive expandable structures such as balloons or other means can be used to ground, anchor and stabilize the proximal section of a catheter containing an occlusion structure that is able to translate about anchor. Manipulation of the occlusion structure about an anchor improves positioning and accuracy by stabilizing, reducing drag and "windup" common to long length catheter systems. Specifically, for the occlusion of LSA ostia, the catheter can be anchored to the ICA (while still allowing blood flow) and allowing the occlusion structure to be precisely advanced into the MCA and up to the LSA ostia with respect to the anchor point.

A method for the hemostasis of perforating and bleeding vessel related ICH includes: navigating an occlusion device in a catheter-based endovascular approach into a parent artery and then deploying the occlusive device in such a manner that the bleeding vessels are transiently occluded until hemostasis is achieved, while maintaining flow within the parent artery. The bleeding arteries are reduced in flow or occluded at their ostia which has several biological effects. Occlusion of the penetrating arteries prevents blood from entering the artery, reducing the blood flow and blood pressure gradient in the perforating bleeding arteries, essentially eliminating the possibility of any further blood loss. While occlusion is one method of treatment, it may be advisable to retain some blood flow through the bleeding vessel. Therefore, the system is adapted to attain partial perforator occlusion to achieve a temporary reduction of blood flow of preferably at least 50%, and potentially 50-70%. The goal is to treat intracerebral hemorrhage by limiting hematoma growth. The temporary occlusion also effectively reduces the mechanical blood pressure forces acting at the site of arterial rupture and thereby less pressure drives blood into brain tissue. This leads to a reduction of blood flow and causing flow to become stagnant, which triggers a coagulation cascade leading to thrombosis that seals the bleeding vessels. Once adequate resolution of hemorrhage has been identified, the operator then recaptures or removes the device from the access route. Specifically, in regards to hemorrhaging LSA, the occlusion device can be navigated into the MCA then deployed up against LSA ostia while maintaining adequate blood flow through the MCA. Additionally, this method can be used to create hemostasis and support the repair of vessels with natural or iatrogenic perforations.

An alternate method includes cyclical occlusion of the hemorrhaging vessels to progressively cause hemostasis and maintain adequate blood flow. This can be accomplished by either temporary retrieval and deployment, or operator driven expansion control of the occluder. Cycling can be user dependent or automatically controlled by a preset or target duty cycle, frequency, quantity and amplitude of occlusion. Additionally, occlusion can be synchronized with cardiac cycle. The total duration of occlusion can be administered in a perioperative or ambulatory fashion.

The occlusion may be adapted to allow partial perfusion to the occluded branched vessels. The purpose of inducing partial hemostasis as opposed to complete hemostasis, is to allow perfusion to continue to ischemia sensitive regions that are typically supplied by the branched vessels. This prevents iatrogenically-induced ischemia while providing adequate hemostasis to reduce hemorrhaging. The materials used to create partial perfusion can have a fixed perfusion rate based on pore sizing or have a variable perfusion rate that is driven by conditions such as blood pressure. Specifically, occluder can be made from ePTFE, processed polymers, fabrics, or other biocompatible materials.

Alternatively, the occlusive material can be engineered to automatically vary the level of its permeability depending on the different hemodynamic affects and composition between hemorrhaging and non-hemorrhaging vessels. In an example, the material is engineered to allow perfusion through non-hemorrhaging vessels and allow no perfusion into hemorrhaging vessels based on their respective internal pressures. This affect can also be supported by introducing different materials in to the blood stream or sensing.

An additional component to the mentioned embodiments as well as any other devices intended to be positioned within a tortuous vascular path is a means to improve positioning accuracy and operator control. Specifically, in cerebral vascular anatomy, it is common to have a path composed of large vessels that are branched at abrupt or acute angles. An example is the abrupt junction between the MCA and the Internal Carotid Artery ICA that are typically observed to be 90 degrees from each other. Therefore, a system that is capable of controlled articulation, advancement and rotation is required to interrogate the LSA ostia located in the MCA by way of ICA. Such system can be composed of a flexible connection member or wire extending out of the main shaft of the device and contains the occlusion system at its distal end. To guide such wire into an abruptly branched vessel, the wire can be supported in a channel that allows for perpendicular deployment. Alternatively, the wire can be guided by a track that can be aligned with the branched artery by articulation.

The embodiments described contain several means of preserving blood flow within the parent partially occluded vessel, however these means are not limited by each embodiment and can be used interchangeably when possible. Alternatively, a means to preserve blood flow in a partially occluded vessel uses forced perfusion via pump mechanism. The systems pump source can be from a mechanized means such as a centrifugal or peristaltic pump or from a hand operated syringe. Alternatively, forced perfusion can be achieved by supplying blood flow directly from or closer to cardiac outflow.

The hemostatic devices deployment and implantation sequence has been described as first inserted into MCA for the purpose of LSA hemorrhage cessation; however, these devices are not limited to these vessels and may be used to generate hemostasis at any communicating site for all feasible branched arteries. As such, anatomical vessels, insertion locations and implantation locations can be used interchangeably wherever logically applicable.

Device designs optionally may incorporate features to allow for the supplemental infusion of substances to promote hemostasis.

The catheter-based systems described herein can be used to stabilize bleeding while performing neurosurgical procedures. Thus, the system combined a catheter-based and neurosurgical-based approach to acute intracerebral hemorrhage treatment. By way of example, it is highly likely that the ultra-early removal of an intracerebral bleed would lessen brain damage. In fact, animal studies have shown that an ultra-early hematoma evacuation results in reduced injury from a brain bleed. A few clinical trials however reported that ultra-early hematoma evacuation was associated with continued bleeding. However, one basis of the invention is an understanding that the catheter-based system prevents bleeding in the intra-operative period. For such purposes, the catheter-based systems are used in the following manner. The device is deployed to the perforating bleeding artery to reduce the blood flow and the pressure gradient on the perforating artery. During this time the patient is prepared for the surgical hematoma evacuation in the operating room and the hematoma is evacuated. The catheter device remains deployed. The surgeon monitors the vascular bed for bleeding. If no bleeding is noted, the device is temporarily collapsed. The angiographer assesses if bleeding has stopped by an injection of angiographic contrast. If no contrast extravasation is observed then the catheter and device is removed. This approach uniquely combines a catheter-based interventional treatment with a neurosurgical treatment for intracerebral hemorrhage, made possible by reducing the blood flow and blood pressure to the surgical field.

Terms such as intracerebral hemorrhage, hemorrhagic stroke, hemorrhage site, hemorrhage, ICH as used herein are the same. Terms such as hemostatic, hemostasis, hemorrhage cessation, hemorrhage occlusion when used herein are the same. Terms such as ostia, branching, communication, communicating site, take-off vessel when used herein are the same. Terms such as vessel, artery, path, tract when used herein are the same. Terms such as catheter, sheath, vascular sheath, hollow tubule, tubule with lumen when used herein are the same.

Various descriptions of the hemostatic devices and of the cessation methods have been used. Each of these descriptions is to be used interchangeably wherever logically applicable and is not to be limited to only one exemplary embodiment described or depicted.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted. To avoid redundancy, repetitive description of similar features may not be made in some circumstances. It shall be understood, however, that description of a first-appearing feature applies to the later described similar feature and each respective description, therefore, is to be incorporated therein without such repetition.

The description and drawings illustrate the principles, exemplary embodiments, and modes of operation of the systems and methods. However, the systems and methods should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the systems and methods as defined by the following claims. Alternate embodiments may be devised without departing from the spirit or the scope of the invention. Additionally, well-known elements of exemplary embodiments of the systems and methods will not be described in detail or will be omitted so as not to obscure the relevant details of the systems and methods.

Further, it is to be understood that the terminology used herein is for the purpose of describing particular embodiments only and is not intended to be limiting. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element. The terms "including" and/or "having," as used herein, are defined as comprising (i.e., open language). The terms "a" or "an", as used herein, are defined as one or more than one. The term "plurality," as used herein, is defined as two or more than two. The term "another," as used herein, is defined as at least a second or more. The description may use the terms "embodiment" or "embodiments," which may each refer to one or more of the same or different embodiments. The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact (e.g., directly coupled). However, "coupled" may also mean that two or more elements are not in direct contact with each other, but yet still cooperate or interact with each other (e.g., indirectly coupled). For the purposes of the description, a phrase in the form "A/B" or in the form "A and/or B" or in the form "at least one of A and B" means (A), (B), or (A and B), where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables, for example, a phrase in the form "at least one of A, B, and C" means (A), (B), (C), (A and B), (A and C), (B and C), or (A, B and C). Relational terms such as first and second, top and bottom, and the like may be used solely to distinguish one entity or action from another entity or action without necessarily requiring or implying any actual such relationship or order between such entities or actions. The description may use perspective-based descriptions such as up/down, back/front, and top/bottom. Such descriptions are merely used to facilitate the discussion and are not intended to restrict the application of disclosed embodiments. Various operations may be described as multiple discrete operations in turn, in a manner that may be helpful in understanding embodiments; however, the order of description should not be construed to imply that these operations are order dependent. As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

What is claimed is:

1. A method for hemostasis of a perforating penetrating artery branching from a mid-cerebral artery (MCA) at an ostia of the perforating penetrating artery and related intracerebral hemorrhage (ICH), comprising:
    navigating an occlusion device in a catheter-based endovascular approach into the MCA, the occlusion device having,
    i) an elongate member with a proximal end and a distal end,
    ii) an expandable member fixed to the distal end of the elongate member, the expandable member sized for insertion into the MCA and having a length sufficient to extend across the ostia, a flow path for blood provided from a proximal side of the expandable member to a distal side of the expandable member, and
    iii) a semi-permeable contacting member about the expandable member; and then
    deploying the occlusion device into contact with a wall of the MCA adjacent the ostia of the perforating penetrating artery to temporarily reduce blood flow from the MCA to the perforating penetrating artery and continuing to allow a portion of blood flow within the flow path to pass through the semi-permeable contacting member to the ostia and into the perforating penetrating artery until hemostasis is achieved,
    while maintaining distal tissue blood perfusion through the MCA via the flow path from the proximal side of the expandable member to the distal side of the expandable member.

2. The method of claim 1, further comprising:
    removing the occlusion device from the parent cerebral artery after hemostasis is achieved.

3. The method of claim 1, wherein deploying includes expanding.

4. The method of claim 1, wherein blood flow is reduced by at least 50%.

5. The method of claim 1, wherein the semi-permeable contacting member is a hemostatic film.

6. The method of claim 1, wherein the contacting member comprises one of ePTFE and PET.

7. A method for hemostasis of a perforating and bleeding vessel related intracerebral hemorrhage (ICH), the vessel branching from a parent cerebral artery at an ostia, the method comprising:
    navigating an occlusion device in a catheter-based endovascular approach into the parent cerebral artery;
    expanding the occlusion device into contact with the ostia of the bleeding vessel until hemostasis is achieved, while permitting a reduced blood flow into the bleeding vessel and while maintaining distal tissue blood perfusion through the parent cerebral artery; and then
    removing the occlusion device from the parent cerebral artery after hemostasis is achieved.

8. The method of claim 7, wherein blood flow is reduced by at least 50%.

9. The method of claim 7, wherein blood flow is reduced by 50-70%.

10. The method of claim 7, wherein the parent cerebral artery is the middle cerebral artery and the bleeding vessel is at least one of the lenticulostriate arteries.

11. The method according to claim 7, further comprising:
    performing a neurosurgical treatment at least within the parent cerebral artery while the occlusion device is within the parent cerebral artery.

12. The method of claim 7, wherein the parent cerebral artery includes an internal carotid artery.

13. The method of claim 7, wherein the parent cerebral artery includes a middle cerebral artery.

14. The method of claim 7, wherein the reduced blood flow into the bleeding vessel passes through a permeable portion of the occlusion device.

15. The method of claim 7, wherein the distal tissue blood perfusion through the parent cerebral artery passes through a flow path within the occlusion device.

* * * * *